US00PP12729P2

(12) United States Plant Patent
Hanes

(10) Patent No.: US PP12,729 P2
(45) Date of Patent: Jun. 25, 2002

(54) GERANIUM PLANT NAMED 'AMRI WHITE SPLA II'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 41 days.

(21) Appl. No.: 09/802,871

(22) Filed: Mar. 12, 2001

(51) Int. Cl.[7] ..... A01H 5/00
(52) U.S. Cl. ..... Plt./325
(58) Field of Search ..... Plt./324, 325

(56) References Cited

U.S. PATENT DOCUMENTS

PP9,317 P * 10/1995 Hanes ..... Plt./325
PP11,397 P * 5/2000 Trees ..... Plt./325

* cited by examiner

*Primary Examiner*—Bruce R. Campell
*Assistant Examiner*—Kent L. Bell
(74) *Attorney, Agent, or Firm*—Rothwell, Figg, Ernst & Manbeck

(57) ABSTRACT

A geranium cultivar particularly distinguished by dark green foliage with light zonation, white flower color, and semi-double flowers on large umbels, fast rooting and exhibits vigorous growth.

1 Drawing Sheet

GENUS AND SPECIES

*Pelargonium hortorum*

VARIETY DENOMINATION

'Amri White Spla II'

BACKGROUND OF THE NEW PLANT

Figure 1:
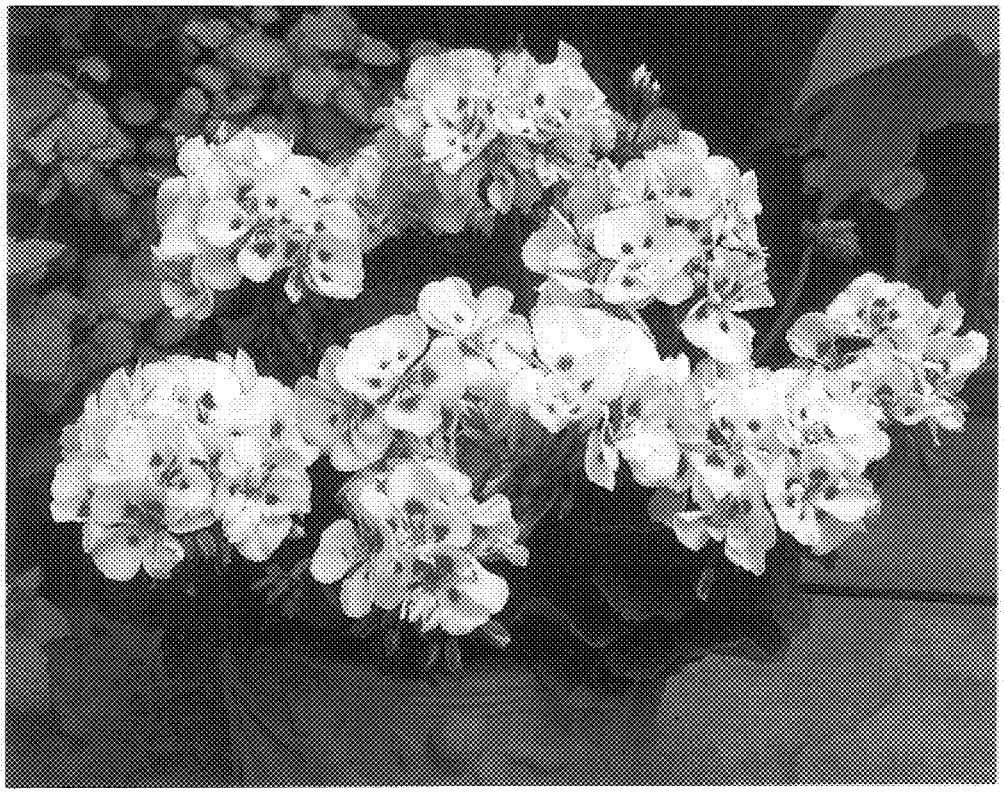

The present invention comprises a new and distinct cultivar of geranium, botanically known as *Pelargonium hortorum* Bailey, and hereinafter referred to by the cultivar name 'Amri White Spla II'. The new cultivar is propagated from a seedling resulting from the cross of an unnamed and unpatented seed parent known as 6196-1 which is a single flowered, white with rose spot pattern line and an unnamed and unpatented pollen parent known as 5621-1 which is a semi-double flowered, white with rose spot pattern line.

'Amri White Spla II' is a product of a planned breeding program intended to create new geranium cultivars with white colored flowers, semi-double flower form, green foliage, vigorous growth and superior cutting productivity.

The new cultivar was created in 1996 in Gilroy, Calif. and has been repeatedly asexually reproduced by cutting in Gilroy, Calif. and Guatemala over a four year period. It has also been trialed at Gilroy, Calif. and Andijk, The Netherlands. It has been found to retain its distinctive characteristics through successive propagations; and this novelty is firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit.

DESCRIPTION OF THE NEW CULTIVAR

The following detailed descriptions set forth the distinctive characteristics of 'Amri White Spla II'. The data which defines these characteristics were collected from asexual reproductions carried out in Gilroy, Calif. The plant history was taken on 5 month old plants blossomed under natural light in a greenhouse and color readings were taken in the greenhouse in Gilroy, Calif. under ambient light. Color references are primarily to The R.H.S. Colour Chart of The Royal Horticultural Society of London (R.H.S.).

DETAILED BOTANICAL DESCRIPTION

Classication:
*Botanical.*—*Pelargonium hortorum* Bailey.
*Commercial.*—Geranium.
Form: Upright, rounded plant.
Height: From soil level to top of plant (excluding blooms) — 17 cm; from soil level to top of umbels — 30–32 cm.
Width: 34–37 cm.
Time to produce a finished flowering plant: 12 weeks.
Outdoor plant performance: Good heat tolerance, strong growth, maintains rounded habit.
Time to initiate roots: 7–8 days.
Time to develop roots: 25 days.
Root description: White, slightly hairy, fibrous yet coarse.

The Leaves

Length: 5.0–6.4 cm.
Width: 7.5–10.0 cm depending on age.
Apex measurement: 3.0 cm.
Apex shape: Rounded.
Base measurement: 6.0–6.5 cm.
Base shape: Cordate.
Shape: Reniform, with occasional upfolding between veins.
Margin: Crenate.
Texture: Leathery and pubescent on both surfaces.
Ribs and veins: Palmate, 3.0–4.5 cm long.

Color:
*Upper side.*—Yellow-green RHS 146A.
*Under side.*—Yellow-green RHS 146B.
*Ribs.*—Yellow-green RHS 146C.
*Veins.*—Yellow-green RHS 146B.
Petiole length: 6.3–10.0 cm.
Petiole diameter: 2.0–3.0 mm.
Petiole color: Yellow-green RHS 146C.
Lateral branch length: 7.0–8.5 cm.
Internode length: 1.5 cm.
Lateral branch color: Yellow-green RHS 146C.

The Bud

Diameter: 0.8 cm.
Length: 1.5 cm.
Shape: Narrow elliptic.
Color when sepals first divide: White RHS 155A.
Number of sepals: 5 linear-lanceolate shaped.
Length of sepals: 1.2 cm.
Width of sepals: 3 mm.
Apex shape: Acuminate.
Base shape: Truncate.
Sepal color: Upper and lower surfaces are yellow-green RHS 144A.

The Flower

Size: Approximately 2.3 cm in diameter and 2.7 cm deep.
Form: Polypetalous, cup shaped, semi-double.
Petals/petaloids: 5–6 petals, 1–2 petaloids; Shape: spatulate.
Apex shape: Obtuse-retuse.
Base shape: Attenuate.
Margin: Entire, undulate.
Petal color:
*Upper surface.*—White RHS 155D with stripes and macules of red-purple RHS 66B on bottom half of upper petal surface.
*Lower surface.*—White RHS 155D with occasional stripes of red-purple RHS 66B near the base of the two top petals.
Petaloid color: Upper and lower surface — white RHS 155D.
Color change with age: None.
Pedicel length: Approximately 2.7–3.0 cm.
Pedicel color: Yellow-green RHS 144A.
Flower persistence: An open flower will hold its petals until the flower begins to dehisce, or approximately 7–10 days.

The Inflorescence

Type: An umbel composed of approximately 11–14 flowers.
Diameter: 7.5–10 cm.
Depth: 6.0 cm.
Peduncle length: 16.5–17.5 cm.
Peduncle color: Yellow-green RHS 144A.

The Reproductive Organs

Anthers: 6–7.
Anther color: Orange-red RHS 35C prior to anthesis.
Filament color: White RHS 155D with a faint stripe of red-purple RHS 66C; filaments are fused to each other except near the anthers.
Pollen amount and color: Moderate, orange RHS 28A.
Pistil: 1 with a length of 1 cm.
Stigma: 5 linear lobes with a color of red-purple RHS 66D.
Style: 2 mm in length with a color of yellow RHS 4D.
Ovary: Densely pubescent.
Seed number: Maximum of 5 per spike.
Seed length: 4.0 mm.
Seed width: 1.0 mm.
Seed color: Brown RHS 165, may darken with age.

Disease and Insect Resistance

No susceptibility to disease or insects noted to date.

Comparison with Known Cultivars

Compared to 6196-1, 'Amri White Spla II' has a semi-double flower form versus a single for the parental cultivar. 'Amri White Spla II' has a more basal branched and stronger growth habit when compared to 5621-1.

I claim:

1. A new and distinct cultivar of geranium plant as shown and described herein.

* * * * *